United States Patent [19]

Martin

[11] 4,222,766
[45] * Sep. 16, 1980

[54] QUATERNARY AMMONIOALKANECARBOXYLIC ACID ANILIDES AS PLANT GROWTH INFLUENCING AGENTS

[75] Inventor: Henry Martin, Allschwil, Switzerland

[73] Assignee: Ciba-Geigy Corporation, Ardsley, N.Y.

[*] Notice: The portion of the term of this patent subsequent to Feb. 27, 1996, has been disclaimed.

[21] Appl. No.: 215

[22] Filed: Jan. 2, 1979

Related U.S. Application Data

[63] Continuation-in-part of Ser. No. 751,616, Dec. 16, 1976, Pat. No. 4,141,718.

[30] Foreign Application Priority Data

Dec. 23, 1975 [CH] Switzerland .................. 16704/75

[51] Int. Cl.$^2$ .................. A01N 9/22; C07D 207/06
[52] U.S. Cl. .................. 71/95; 260/326.43
[58] Field of Search .................. 260/326.43; 71/95

[56] References Cited

U.S. PATENT DOCUMENTS 4,162,322  7/1979  Malen .................. 424/267

Primary Examiner—Donald G. Daus
Assistant Examiner—Lisa Jones
Attorney, Agent, or Firm—Frederick H. Rabin

[57] ABSTRACT

This invention comprises new compounds as well as a composition and method for influencing, in particular for inhibiting plant growth, which composition contains as active ingredient a quaternary pyrrolidinium acetic acid anilide of the formula

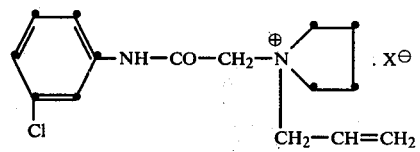

wherein $X^\ominus$ represents the anion of any non-phytotoxic acid.

Methods for manufacturing the bromide of this compound are described and its use for inhibiting the growth of plants, in particular ornamentals.

11 Claims, No Drawings

QUATERNARY AMMONIOALKANECARBOXYLIC ACID ANILIDES AS PLANT GROWTH INFLUENCING AGENTS

Cross-reference to related application

This is a continuation-in-part of my copending application Ser. No. 751,616, filed Dec. 16, 1976, now U.S. Pat. No. 4,141,718.

DETAILED DESCRIPTION

The present invention provides compositions for regulating, in particular for inhibiting plant growth which contain as active components quaternary salts of pyrrolidinium acetic acid anilides and a method of regulating plant growth which comprises the use of these active compounds and compositions which contain them. The invention also provides novel quaternary salts of pyrrolidinium acetic acid anilides and a process for their manufacture.

A substantial number of quaternary aminoacetic anilides and pyridinioacetic anilides which possess pharmaceutical, disinfectant and bactericidal-fungicidal action etc. are known from the literature, but no particulars are provided relating to any positive and inhibiting action of these compounds with regard to plant growth. From the extensive literature, attention is drawn here only to a number of references, such as "Nature" 216, 1331–33 (1967), 223, 748 (1969); Europ. J. Pharmacology 13, 46 (1970); DOS 2 351 942; British Pat. No. 688,604; Journ. hterocycl. Chem., 8, 1079 (1971); Gazz. Chim. Ital. 95, 1237 (1965); Tetrahedron letters 1969, 4945 etc.

Certain quaternary aminoacetic anilides have already been suggested for different technical purposes, for example as moth repellents (U.S. Pat. No. 2,343,071 and German Reichspatent No. 905,373 etc.).

None of these publications contains the remotest allusion to or indication of a plant growth-influencing action of such known compounds.

On the other hand, quaternary ammonium compounds having another structure are on the market as plant regulators and are described in detail for example in R. Wegler's "Chemie der Pflanzenschutz- und Schädlingsbekämpfungsmittel", vol. 2, Springer Verlag, 1970, pp. 323–326 and 407, with reference to the original literature.

Further quaternary ammonium compounds with a plant growth-regulating action have become known for example from Ann. Appl. Biol. 63, 211 (1969); from U.S. Pat. Nos. 3,701,799; 3,580,716; 3,856,850 and 3,895,933, and from the Journ. Agr. and Food Chem. 7, 264 (1959) and 16, 523 (1968). However, all these prior art growth-regulators are not quaternary ammonioalkanoic acid anilides, but are to some extent very complicated organic compounds.

The present invention is based on the surprising observation that quaternary salts of pyrrolidinium acetic acid anilides of the formula I

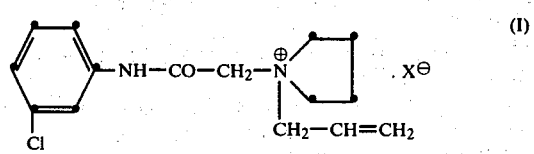

(I)

wherein X represents the anion of any non-phytotoxic acid HX, possess outstanding plant growth-regulating properties in mono- and especially dicotyledonous plants, and can be used for example as growth inhibitors for grasses, cereals, soya beans, ornamentals, fruit etc., and also have some abscission effect on fruit and leaves.

The anion X can be selected from any of the non-phytotoxic acids and has no appreciable influence on the biological action. X is for instance chlorine, bromine or iodine.

According to the present invention, the novel salts of the formula I are obtained by methods which are known per se by reacting 3-chloro-aniline with a reactive halogenacetic acid derivative to give a halogenoacetic acid anilide of the formula

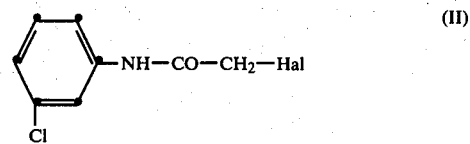

(II)

and then reacting this compound with pyrrolidine and converting the resultant pyrrolidino acetic acid anilide with a quaternising agent introducing the allyl group besides a non-phytotoxic anion.

The intermediates of the formula II are obtained by treating 3-chloro-aniline with halogen-substituted acetic acid or suitable derivatives, such as the esters, halides, amides or anhydrides thereof, the prefered derivative is chloroacetylchloride.

The reaction of the halogen-substituted aceticacid anilides of the formula II with pyrrolidine is carried out by known methods to form by dehydrohalogenation the corresponding acetic acid anilide.

The subsequent aftertreatment with the quaternising agent provides quaternary substitution of the nitrogen atom. This quaternisation is customarily performed with a mineral acid ester of allyl alcohol such as an allyl halide or diallyl sulphate. Allyl chloride and allyl bromide are the prefered quaternising agents.

The quaternary salts of the formula I possess the plant growth-regulating section, in particular a plant growth-retarding action.

Accordingly, compounds of the formula (I) can be used for controlling the growth of plants in agriculture and in horticulture. A variety of typical methods of application is listed hereinafter:

For reducing the labour and expense involved in cutting by inhibiting the herbaceous soil covering on road shoulders, canal embankments, in airports, fruit plantations, on turf for sporting activities and ornamental grass plots etc., and for inhibiting the growth of shoots of bushes, hedges, ornamental bushes, fruit and other trees.

For inhibiting unwanted suckers in tobacco plants and other cultures.

For increasing the yield in cultures of leguminosae (for example soya and ground nuts) by inhibiting the vegetative growth in favour of the generative growth.

For increasing the stability of crops of plants which are susceptible to lodging, such as cereals, maize and soya (preventing the plants from being flattenedunder unfavourable weather conditions).

For inhibiting the excessive growth of ornamentals which are reared in pots, such as chrysanthemums, poinsettia, etc.

For increasing the blossoming of cultivated plants, for example young fruit trees.

For speeding up the ripening of fruit.

For facilitating the harvesting of fruit by promoting the formation of separation tissue between the fruit and the shoots of the plants.

The quaternary ammonium salts of the formula (I) are used in the form or preparation which, in addition to containing the quaternary ammonium salt of the formula (I), also contain a carrier or a surface-active agent or a carrier and a surface-active agent. The effectiveness of the quaternary ammonium salts of the formula (I) depends on the concentration when they are used as plant growth-regulators. In addition, substantial variations with regard to the active concentration of the quaternary ammonium salts of the formula (I) as plant growth-regulators are possible, this concentration being dependent not only on the species, organism or nature of the plants to be treated, but also on the physiological age of the plants. The cocentration to be applied should therefore be selected depending on the composition employed, the species of plant, and the duration of the application. In general, effective concentrations are in the range between 1 and 5000 ppm and preferably between 10 and 500 ppm. However, these values are of no particular importance.

The active compounds of the formula (I) can be used by themselves or in combination with other regulators, with trace elements, chelates, fertilisers, and also with fungicides, insecticides and acaricides. Furthermore, stabilisers can also be added to the active compounds and the compositions which contain them.

The following Example illustrates the manufacture of an active salt of formula I.

EXAMPLE 255.2 g (2 moles) 3-chloroaniline are dissolved in 500 ml of acetone and then a solution of 246 g (3 moles) of sodium acetate in 800 ml of water is added thereto. With stirring, 190 ml (2.5 moles) of chloroacetyl chloride are added tropwise to the mixture in the course of 3 hours while keeping the temperature at 35° to 55° C. When the addition is complete stirring of the obtained suspension is continued for a further 2 hours at room temperature and thereafter 400 ml of ice-water are added whereby the suspension becomes thick. After the batch is cooled to 5°–10° C., the formed chloroacetyl-3-chloro-aniline is collected with suction, washed thoroughly with water and dried in vacuo at 50° C.

Yield: 395.2 g=96.6% of theory. Melting point: 99°–101° C.

152.7 g (0.75 mole) of chloroacetyl-3-chloro-aniline are dissolved in 300 ml of absolute ethanol and then 160.0 g (2.25 moles) of pyrrolidine are slowly added (exothermic reaction) and the mixture is then boiled under reflux for 5 hours with stirring. The crude product is then concentrated in vacuo (Rotavap), and the concentrate dissolved in methylene chloride, washed twice with water and the extract (methylene chloride phase) is dried over Na$_2$SO$_4$. After filtration, the solution is concentrated by evaporation under vacuo. Yield: 170.4 g of pyrrolidino acetic acid 3-chloro-anilide in form of a brown oil (95.1% of theory). The oil solidifies after some days and the solid product melts at 51°–54° C.

14.3 g (0.06 mole) of pyrrolidinoacetic acid 3-chloroanilide are dissolved in 50 ml of ethyl acetate and then 9.4 g (0.078 mole) of allyl bromide are added. The reaction mixture is refluxed for 3 hours and the quaternised end product initially separates out as an oil which chrystallises after a brief time. After filtration with suction, washing with ethyl acetate and drying in vacuo at 50° C., 21.5 g (99.5% of theory) of the quaternary allyl pyrrolidino bromide of the formula

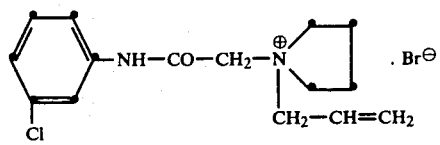

are obtained. Melting point: 144°–147° C. The product is colourless, soluble in water (3.7%) and methanol (30%) and stable against hydrolysis in all pH-ranges from 3 to 10.

Other non-phytotixic salts may be prepared in an analogous manner, for example the chloride and iodide.

From these halides, other non phytotoxic salts may be prepared by known methods, such as the nitrate, sulfonate, trifluoromethanesulphonate, the sulphate, chlorate, acetate, borate, tartrate, succinate, phosphate etc.

The compositions according to the invention are obtained in known manner by intimately mixing and/or grinding active substances of the formula I with suitable carriers, with or without the addition of dispersants or solvents which are inert towards the active substances. The active substances may take and be used in the following application forms:

Solid forms:
dusts, tracking agents, granules, coated granules, impregnated granules and homogeneous granules;
active substance concentrates which are dispersible in water;
wettable powders, pastes, emulsions; emulsion concentrates.

Liquid forms: solutions.

Solid forms (dusts, tracking agents, granules) are obtained by mixing the active substances with solid carriers. Suitable carriers are, for example: kaolin, talc, bolus, loess, chalk, limestone, ground limestone, atta-clay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The granular size of the carriers for dusts is advantageously up to approx. 0.1 mm, for tracking agents approx. 0.075 to 0.2 mm., and for granules 0.2 mm or greater.

The concentrations of active substance in the solid forms are 0.5 to 80%.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable aggentiants are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, lignin sulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents. The concentrations of active substance in these compositions is 5 to 80%.

Wettable powders and pastes are obtained by mixing and grinding the active substances with dispersing agents and pulverulent carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali metal, ammonium and alkaline earth metal salts of lignin sulphonic acid, in addition, alkylaryl sulphonates, alkali metal and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetalene glycols, dialkyl dilauryl ammonium chloride and fatty acid alkali metal and alkaline earth metal salts.

Suitable anti-foam agents are for example silicones.

The active substance is so mixed, ground sieved and strained with the additives mentioned above that, in wettable powders, the solid particle size of 0.02 to 0.04 mm and in pastes, of 0.03 mm, is not exceeded. Emulsion concentrates and pastes are manufactured by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active substances and not readily inflammable.

Furthermore, the agents according to the invention can be applied in the form of solutions. For this purpose the active substances or several active substances of the general formula I are dissolved in suitable organic solvents, mixtures of solvents, or in water. Aliphatic and aromatic hydrocarbons, chlorinated derivatives thereof, alkylnaphthalenes and mineral oils, by themselves or in admixture, can be used as organic solvents. The solutions will contain the active substances in a concentration from 1 to 20%.

These solutions can be applied either by means of a propellant gas (as spray) or with special sprays (as aerosol).

The compositions of this invention can be mixed with other biocidally active substances or agents. Thus in order to broaden the activity spectrum the compositions may contain, for example, insecticides, fungicides, bactericides, fungistats, bacteriostats or nematocides, in addition to the cited compounds of the formula I. The compositions of the invention may also contain plant fertilisers, trace elements etc. Formulations of one of the novel active compounds of the formula I are described hereinafter. The parts denote parts by weight.

Granules

The following substances are used to produce 5% granules:
5 parts of the bromide of the Example,
0.25 parts of epichlorohydrin,
0.25 parts of cetyl polyglycol ether,
3.50 parts of polyethylene glycol ("Carbowax"),
91 parts of kaolin (particle size 0.2–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

The resultant granules are particularly suitable for incorporation into the soil which is intended for rearing ornamental plant cuttings whose growth is to be inhibited.

Wettable powder

The following constituents are used for the preparation of (a) a 40%, (b) a 50%, (c) a 25%, and (d) a 10% wettable powder:

(a)

40 parts of the compound of the Example
5 parts of sodium lignin sulphonate,
1 part of sodium dibutyl-naphthalene sulphonate,
54 parts of silicic acid.

(b)

50 parts of the foresaid active substance,
5 parts of alkylarylsulphonate ("Tinovetin B"),
10 parts of calcium ligninsulphonate,
1 part of a mixture of Champagne chalk/hydroxyethyl cellulose mixture (1:1),
20 parts of silicic acid,
14 parts of kaolin.

(c)

25 parts of the active substance,
5 parts of the sodium salt of oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin. (d)
10 parts of the active substance,
3 parts of a mixture of the sodium salts of saturated fatty alcohol sulphates,
5 parts of naphthalenesulphonic acid/formaldehyde condensate,
82 parts of kaolin.

The active substance is homogeneously mixed in suitable mixers with the additives and the mixture is then ground in appropriate mills and rollers. Wettable powders are obtained which can be diluted with water to give suspensions of the desired concentration. Such suspensions can be used for example for inhibiting the growth of soya, cuttings, ornamentals etc.

Emulsion Concentrate

The following ingredients are mixed to prepare 25% emulsion concentrates:

(a)

25 parts of the active substance,
5 parts of a mixture of nonylphenolpolyoxyethylene and calcium dodecylbenzenesulphonate,
70 parts of xylene.

(b)

25 parts of the active substance,
10 parts of a mixture of nonylphenolpolyoxyethylene and calcium dodecylbenzenesulphonate,
65 parts of cyclohexanone.

This concentrate can be diluted with water to give suitable concentrations. Such emulsions are suitable for inhibiting the growth of dicotyledonous plants such as soyabeans, ornamentals etc. As has already been mentioned, the compositions of the present invention are suitable for inhibiting the vegetative growth especially of dicotyledonous plants by imparting a more compart form to these plants. The active compounds of the compositions have only a low toxicity to warm-blooded animals (LD$_{50}$ rat peroral: 1313 mg/kg; LD$_{50}$ rat dermal: >3100 mg/kg). When used in reasonable amounts, the quaternary salts cause no damage to the plants. The novel compositions and the active compounds contained therein retard the vegetative growth, promote blossoming, the ripening of fruit and to some extend also the formation of separation tissue.

The principal field of use of these compositions of the present invention is the inhibition of growth in cultures of soya and other leguminosae, and particularly in ornamentals, bushes (hedgerows) and trees.

By inhibiting growth it is possible, for example, to sow the plants in soya cultures in more narrowly spaced rows, which in turn makes a greater yield possible per unit of area. The plants are of smaller growth, develop strong green leaves and, in proportion to the leaves, a greater blossoming and set of fruit. The tighter spacing of the plants affords better protection against their being beaten to the ground by rain and wind.

In tobacco plants, the growth inhibition prevents chiefly the formation of side-shoots or suckers, a factor which aids the development of large strong leaves.

The application of the compositions of the invention effects in grasses, especially in southern warm season grasses, a slower growth, whereby for example areas of grass need be cut less often.

The growth inhibition of ornamental plants and shrubs results in smaller plants of regular proportions with shorter stalks. Ornamentals shrubs require less frequent cutting.

The extent and nature of the action depend on a wide variety of factors according to the species of the plant, in particular on the application concentration, and the time of application with regard to the development stage of the plant. The active substances are applied preferably in the form of liquid compositions both to the parts of plants above the soil and to those on or in the soil. The application to the parts of plants above the soil is preferred, for which purpose solutions or aqueous dispersions are most suitable.

The rates of application must be adapted to the cultivated plant, the time of application and are advantageously between 0.01 and 2 kg per hectare.

Inhibition of the vegetative growth and yield increase of soya plants

Soya plants of the variety "Hark" were reared in earthenware pots and sprayed at the 5-trifoliate leaf stage with aqueous preparations of the active substance of the Example. The active substance concentrations in the spray broth were 500, 100 and 50 ppm respectively. The plant growth was evaluated 4 weeks after application in accordance with the following linear rating:
1 = strong inhibition (no growth from the time of application)
9 = no inhibition (growth as untreated controls)

The yield increase was evaluated at the sime time in percent increase of the pods when compared with the yield of pods obtained with untreated control plants.

Value A expresses the % increase in number of pods.
Value B express the % increase in weight of pods.

| Inhibtion rating | | | % increase of pods | | | | | |
|---|---|---|---|---|---|---|---|---|
| 500 ppm | 100 ppm | 50 ppm | 500 ppm | | 100 ppm | | 50 ppm | |
| | | | A | B | A | B | A | B |
| 6 | 7 | 6 | 2 | 0 | 22 | 11 | 45 | 43 |

The compounds of formula I do not belong to the most active growth inhibitors but are well dosable weak growth inhibitors. This fact and especially the circumstance that the activity is highly dependant from the rates used render the active igredients of formula I particularly suitable for use in horticulture: Any desired height of Chrysanthema, poinsetta and other ornamentals including hedges can be pre-determinated by a gardener cultivating big areas of these flowers, conforming to the choice of the treating dosage.

As chrysanthema, poinsettia etc., when cultivated without the use of plant-growth inhibitors, attain a height, when flowering, which is to big for being put in housing spaces as ornamentals. Therefore in horticulture the aim is to cultivate, on a large scale, ornamentals of smaller size without affecting the flowers with respect to size and beauty. Normally a height reduction of 20 to 35% is desired and should be predictible by the rates of plant growth inhibitor used.

The known growth inhibitor Alar ® which is succinic acid mono-N-dimethylhydrazide (Daminozide) of formula

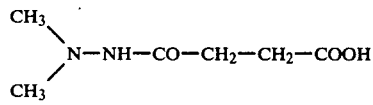

has the disadvantage of high prize, high dosage rates necessary for obtaining the desired growth reduction effect (3000 to 5000 ppm) and the fact that the activity depends very critically on the dosage rate, the activity increasing considerably when a somewhat higher dosage rate is used.

Therefore the desired height of ornamentals is difficult to predeterminate. Furthermore Alar ® is only taken up by the leaves and therefore cannot be applied to the soil (no root uptake) by drench or granule application.

The quaternary salts of the present invention do not have these drawbacks: they are lower in prize, the necessary dosage rate for attaining a 20 to 35% reduction of the height of the ornamentals is between 100 and 500 ppm and the desired activity (growth reduction) can be well predetermined by the choice of the dosage rate: when a standard rate is doubled the growth reduction effect becomes 5 to 10% higher. Therefore for a specific ornamental any desired height to achieve after a certain time can be predeterminated by the choice of the dosage rate. The quaternary salts of the invention furthermore may be applied both by the leaves (foliar spray) as through the roots by drench or granule application to the soil.

Trials under practical conditions on chrysanthemums have shown that the compound of the Example causes a uniform and reproducible inhibition of internode growth. This inhibition is independent of environmental conditions (e.g. it is not light-dependent). Depending on the applied rate, any desired degree of growth inhibition can be obtained.

The leaf size of treated plants is not reduced and the leaves are deeper green.

Even with strong overdoses, no phytotoxicity in the form of necrosis has been observed. However, an increased delay of flowering may occur (2 to 3 days).

Biological Tests on Chrysanthemums

In these tests chrysanthemum varieties were used which, on account of their strong growth, can only be reared as pot plants in combination with growth inhibitors.

About 25 days after potting (14 days after pinching) the plants were sprayed with aqueous preparations of the active substance of the Example and with Alar (known inhibitor for comparison). The dosage rates are indicated in the following tables. The growth in height of the plants was measured after three different periods (see table) and the growth inhibition is expressed in percent of the height measured on untreated plants (check=0% reduction).

Depending on the variety the optimal growth inhibition (20 to 35%) was obtained with rates between 125–250 ppm of the active ingredient of the Example in sufficient water to wet all the foliage. With one variety a soil drench application was also performed.

The following tables show the performance of the quaternary salt of the Example of this specification:

(Compound B)

on different chrysanthemum varieties compared with the standard compound Daminozide or "Alar ®"

(Compound A)

$$CH_3\diagdown N-NH-CO-CH_2-CH_2-COOH$$
$$CH_3\diagup$$

The delay in flowering was evaluated as follows:
*=3–4 days delay
**=4–7 days delay
DAA=Days after application
No phytotoxicity occured in any trial.

Table I

| | Chrysanthemum variety "Regal Anne" | | | |
|---|---|---|---|---|
| | rate | height reduction against check | | |
| Compound | ppm | 11 DAA | 30 DAA | 55 DAA |
| A foliar spray | 3400 | 40% | 40% | 25%* |
| B foliar spray | 125 | 10% | 25% | 25%* |
| | 250 | 25% | 50% | 25%* |
| | 500 | 25% | 60% | 40%* |
| | 1000 | 25% | 60% | 40%* |
| | 2000 | 40% | 75% | 50%** |
| B Soil drench | 250 | 25% | 50% | 50%** |

Table II

| | Chrysanthemum variety "Golden Anne" | | | |
|---|---|---|---|---|
| | rate | height reduction against check | | |
| Compound | ppm | 14 DAA | 32 DAA | 39 DAA |
| A foliar spray | 3400 | 30% | 30% | 25%* |
| B foliar spray | 125 | 10% | 30% | 20%* |
| | 250 | 20% | 35% | 30%** |
| | 500 | 30% | 40% | 35%** |

Table III

| | Chrysanthemum variety "Aglow" | | | |
|---|---|---|---|---|
| | rate | height reduction against check | | |
| Compound | ppm | 14 DAA | 32 DAA | 39 DAA |
| A foliar spray | 3400 | 20% | 30% | 25%* |
| B foliar spray | 125 | 0% | 0% | 10%* |
| | 250 | 10% | 10% | 25%* |
| | 500 | 15% | 25% | 30% |

| | Chrysanthemum variety "Wedgewood" | | | |
|---|---|---|---|---|
| | rate | height reduction against check | | |
| Compound | ppm | 14 DAA | 32 DAA | 39 DAA |
| A foliar spray | 3400 | 30% | 30% | 25%* |
| B foliar spray | 125 | 10% | 10% | 20%* |
| | 250 | 15% | 15% | 25%* |
| | 500 | 15% | 25% | 25%* |

The recommended rates for chrysanthemum varieties are:
 foliar spray: 100–500 ppm of compound B of the Example
 soil deach: not higher than 250 ppm
Similar good results are obtainable also on poinsettias and salvia spp.

For poinsettias the rates should be 2 to 4 times higher than for chrysanthemum, i.e. 200 to 2000 ppm for foliar spray.

I claim:
1. A compound of the formula

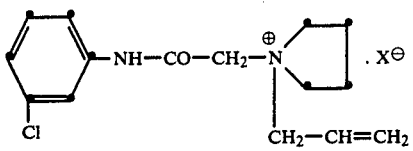

wherein X is the anion of any non-phytotoxic acid.

2. A compound according to claim 1 in which X is chlorine or iodine.

3. The compound according to claim 1 wherein X is bromine.

4. A composition for inhibiting the growth of dicotyledonous plants which comprises (1) a compound according to claim 1 and (2) a carrier.

5. A composition for inhibiting the growth of dicotyledonous plants which comprises (1) the compound according to claim 3 and (2) a carrier.

6. A method for inhibiting the growth of dicotyledonous plants which comprises applying thereto a growth inhibiting effective amount of a compound according to claim 1.

7. A method for inhibiting the growth of dicotyledonous plants which comprises applying to the leaves of the plants or to the soil where these plants are reared a growth inhibiting effective amount of the compound according to claim 3.

8. A method for inhibiting the growth of ornamental plants which comprises applying thereto, after emergence, a growth inhibiting effective amount of a compound according to claim 1.

9. A method for inhibiting the growth of ornamental plants which comprises applying, after emergence, to the leaves of the plants or to the soil where these plants are reared, a growth inhibiting effective amount of the compound according to claim 3.

10. A method for inhibiting the vegetative growth of soya plants which comprises applying thereto a growth inhibiting effective amount of a compound according to claim 1.

11. A method for reducing the height of growing chrysanthemum plants which comprises spraying the leaves of the plants until run-off with an aqueous preparation containing from 100 to 500 ppm of the compound according to claim 3.